US00PP07854P

United States Patent [19]

Jessel, Jr.

[11] Patent Number: Plant 7,854

[45] Date of Patent: Apr. 14, 1992

[54] CARNATION PLANT NAMED 'CFPC LEMON TWIST'

[75] Inventor: Walter H. Jessel, Jr., Salinas, Calif.

[73] Assignee: California Florida Plant Co., L.P., Salinas, Calif.

[21] Appl. No.: 580,197

[22] Filed: Sep. 10, 1990

[51] Int. Cl.[5] ..... A01H 5/00

[52] U.S. Cl. ..... Plt./70

[58] Field of Search ..... Plt./70

[56] References Cited

U.S. PATENT DOCUMENTS

P.P. 5,544 8/1985 van Andel ..... Plt. 70
P.P. 6,273 9/1988 Barberet et al. ..... Plt. 70
P.P. 6,704 3/1989 Klemm ..... Plt. 70

*Primary Examiner*—Howard J. Locker
*Attorney, Agent, or Firm*—Christie, Parker & Hale

[57] ABSTRACT

A new and unusual miniature carnation of pale yellow coloration.

1 Drawing Sheet

BACKGROUND OF THE INVENTION

Carnation varieties producing flowers of many different colors are well known. However, it is desirable to provide a new miniature variety of carnation producing pale yellow flowers.

The closest variety to mine of which I am aware is the variety known as 'Lek's Adelfie'. 'CFPC Lemon Twist' differs therefrom in producing flowers with a diameter averaging ½-inch smaller and pinched plants which are two to three inches shorter, both of which characteristics are especially significant in a miniature variety.

SUMMARY OF THE INVENTION

The present invention relates to a new and distinct variety of carnation plant which was originated by me in a controlled breeding program by my crossing as seed parent, the variety known as 'Lior' and as pollen parent, a numbered but unnamed and unpatented seedling of my creation. The varietal denomination of this new carnation is 'CFPC Lemon Twist'.

Among the novel characteristics possessed by the new variety which distinguish it from its parents and all other varieties of which I am aware are its early flowering response, lack of splitting and non-brittle stems.

Asexual reproduction by propagation by side shoot cuttings of the new variety as performed in Fremont, and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development (tight bud, partially opened bud and full bloom), depicted in color as nearly true as it is reasonably possible to make the same in a color illustration of this character.

DESCRIPTION OF THE NEW VARIETY

The new variety 'CFPC Lemon Twist', produces strong, straight, medium-sized sprays of flowers which are long lasting after cutting, on a very vigorous and free-breaking plant. The foliage is long and straight at the base of the plant. The new variety also has a strong calyx with very little splitting; therefore, taping or banding is not necessary.

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, and Salinas, Calif. The height of plant and flower and foliage size are established as an average using standard commercial cultural practices.

Name: CFPC Lemon Twist.
Classification:
*Botanical.*—*Dianthus caryophyllus.*
*Commercial.*—Greenhouse type, suitable for cut flower production as a spray.
Parentage:
*Female parent.*—'Lior'.
*Male parent.*—Unnamed seedling (No. 0036).

PLANT

Height: About 39 to 40 inches.
Growing habit: Herbaceous, semi-upright.
Blooming habit: Terminal as a spray.
Blooming season: Year round.
Rooting time: 16–18 days.
Mutation prone: No.
Disease resistance: Unknown.
Temperature tolerance: Typical for carnation.

FOLIAGE

Color:
*Upper side.*—Near to 137A.
*Lower side.*—Near to 137A.
Size: About 5½ inches long, about ½-inch wide at base of plant.
Quantity: Numerous.
Shape: Lanceolate.
Texture: Smooth.
Ribs: Central keel.

Arrangement: Bi-lateral along stem.
Stem:
*Color.*—Green.

BUD

Shape: Oval.
Color: Near to 143A.
Length: About $\frac{7}{8}$ inch.
Diameter: About $\frac{2}{3}$ inch.

CALYX

Number of lobes (sepals): About 6.
Length: About 1 inch.
Width: About $\frac{2}{3}$ inch.
Color: Outside — near to 143A. Inside — near to 138D.

BLOOM

Shape: Round.
Size:
*Diameter average.*—About $1\frac{3}{4}$ to $2\frac{1}{8}$ inches.
Borne: Terminal as a spray.
Color:
*General tonality.*—Yellow with occasional light pink and white markings. When present, the light pink markings are lighter than 56D and the white markings are whiter than 155D.
*Upper side.*—Near to 1D.
*Lower side.*—Near to 2D.
*Center.*—Near to 1D.
*Outer petals.*—Near to from 1D to 2D.
Permanence: Yes.
Keeping habit: 12 to 15 days.
Fragrance: Slight.

PETALS

Number: About 38–40.
Texture: Smooth.
Form: Fan shaped.

REPRODUCTIVE ORGANS

Stamen:
*Number.*—About 15–18.
*Arrangement.*—Around the ovary.
Anthers:
*Number.*—About 15–18.
*Length.*—About $\frac{1}{4}$ to $\frac{3}{8}$ inch.
*Color.*—Near to 156D.
Filaments:
*Lengths.*—About $\frac{1}{2}$ inch.
*Color.*—Near to 155D.
Pistil:
*Number.*—About 2.
*Length.*—About $\frac{3}{4}$ to $1\frac{1}{4}$ inches.
*Color.*—Style — near to 159B.
Stigma:
*Number.*—About 2.
*Color.*—Near to 159C.
Fertility:
*Male.*—Very poor.
*Female.*—Unknown.
Ovary:
*Shape.*—Conical, ribbed.
*Color.*—Base — greenish white. Body — greenish yellow. Apex — tan.

I claim:

1. A new and distinct variety of miniature carnation plant, substantially as shown and described, characterized particularly by flowers borne in sprays of pale yellow coloration.

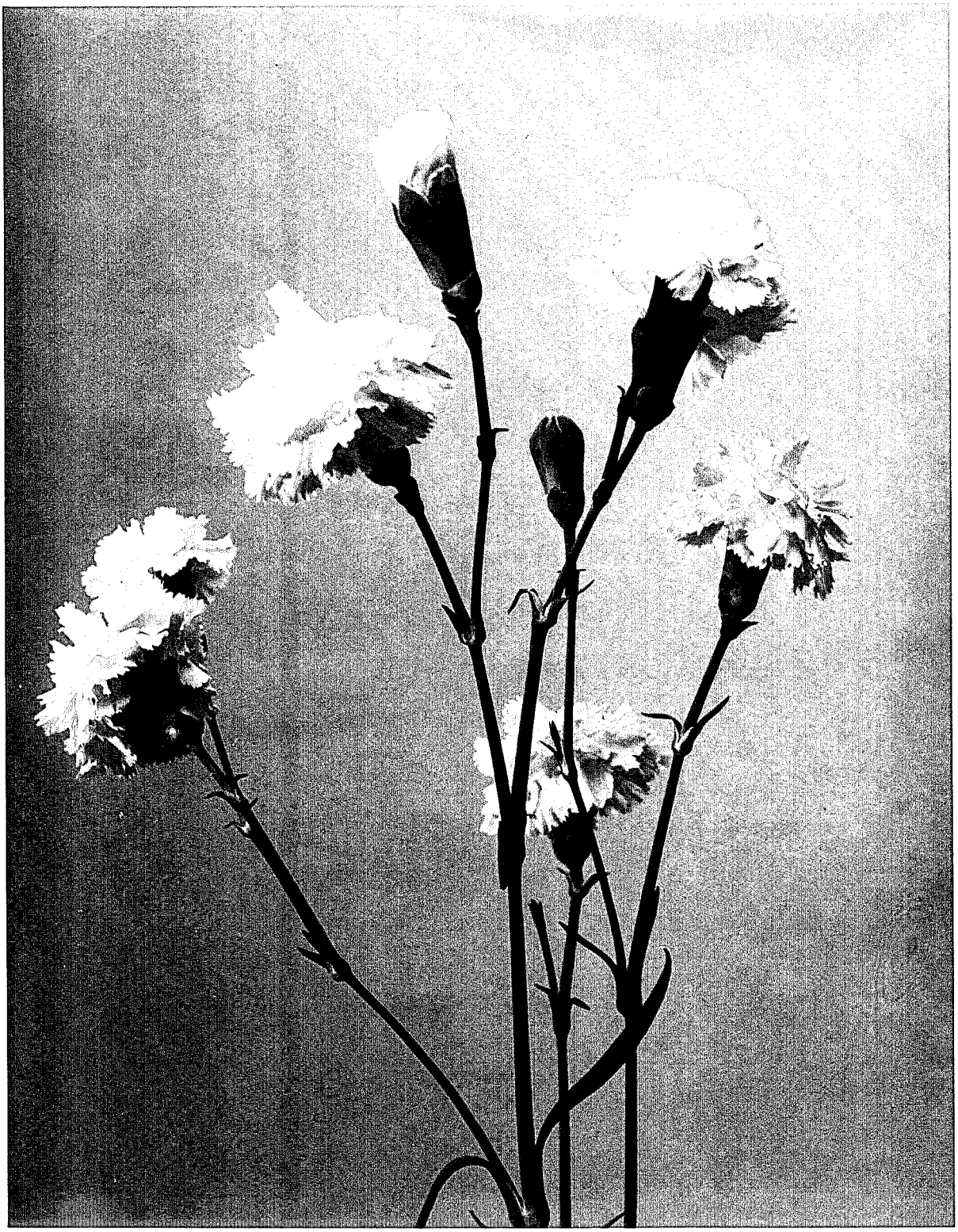

* * * * *